US010468666B2

(12) United States Patent
Liu et al.

(10) Patent No.: US 10,468,666 B2
(45) Date of Patent: Nov. 5, 2019

(54) ROLLING PRESS AND CONDUCTIVITY DETECTOR FOR THE MANUFACTURE OF LITHIUM-ION BATTERY ELECTRODES

(71) Applicant: Nissan North America, Inc., Franklin, TN (US)

(72) Inventors: Ying Liu, Walled Lake, MI (US); Taehee Han, West Bloomfield, MI (US); Yoshitaka Uehara, Novi, MI (US)

(73) Assignee: Nissan North America, Inc., Franklin, TN (US)

(*) Notice: Subject to any disclaimer, the term of this patent is extended or adjusted under 35 U.S.C. 154(b) by 470 days.

(21) Appl. No.: 15/280,588

(22) Filed: Sep. 29, 2016

(65) Prior Publication Data

US 2018/0090742 A1 Mar. 29, 2018

(51) Int. Cl.
*H01M 4/04* (2006.01)
*G01N 27/02* (2006.01)
*H01M 4/139* (2010.01)

(52) U.S. Cl.
CPC .......... *H01M 4/0435* (2013.01); *G01N 27/02* (2013.01)

(58) Field of Classification Search
CPC ... H01M 4/0435; G01N 27/04; G01N 27/045; G01N 27/041; G01N 2030/645; B21B 38/00–12
USPC .............. 72/6.1–14.8, 252.5, 17.3, 365.2
See application file for complete search history.

(56) References Cited

U.S. PATENT DOCUMENTS 5,455,514 A * 10/1995 Pazda ................... G01N 27/60
  324/452
2017/0256781 A1* 9/2017 Suzuki ................ H01M 4/0404

FOREIGN PATENT DOCUMENTS

EP 1231652 A1 8/2002
KR 101462429 B1 * 11/2014

OTHER PUBLICATIONS

Translation of KR-101462429-B1 (Year: 2014).*
MTI Corporation, Electric Precision 6" Width Rolling Press with Dual Micrometer—MSK-2120, http://www.mtixtl.com/ElectricPrecision6WidthRollingPresswithDualMicrometer-msk-2150.aspx, printed Jul. 22, 2016.
ULVAC Technologies, Inc., Plate Press with Conductivity Detector—Product Specification TER-2000SS, pp. 1-6, Jun. 21, 2016.

* cited by examiner

*Primary Examiner* — Elaine Gort
*Assistant Examiner* — Christopher B Wehrly
(74) *Attorney, Agent, or Firm* — Young Basile Hanlon & MacFarlane, P.C.

(57) ABSTRACT

A rolling press for the manufacture of a battery electrode includes a first roller of a non-conductive material, a base of a non-conductive material spaced from the first roller equal to a desired thickness of the battery electrode, and a conductivity detector having a first electrode configured to contact a first side of the battery electrode and a second electrode configured to contact a second side of the battery electrode.

12 Claims, 5 Drawing Sheets

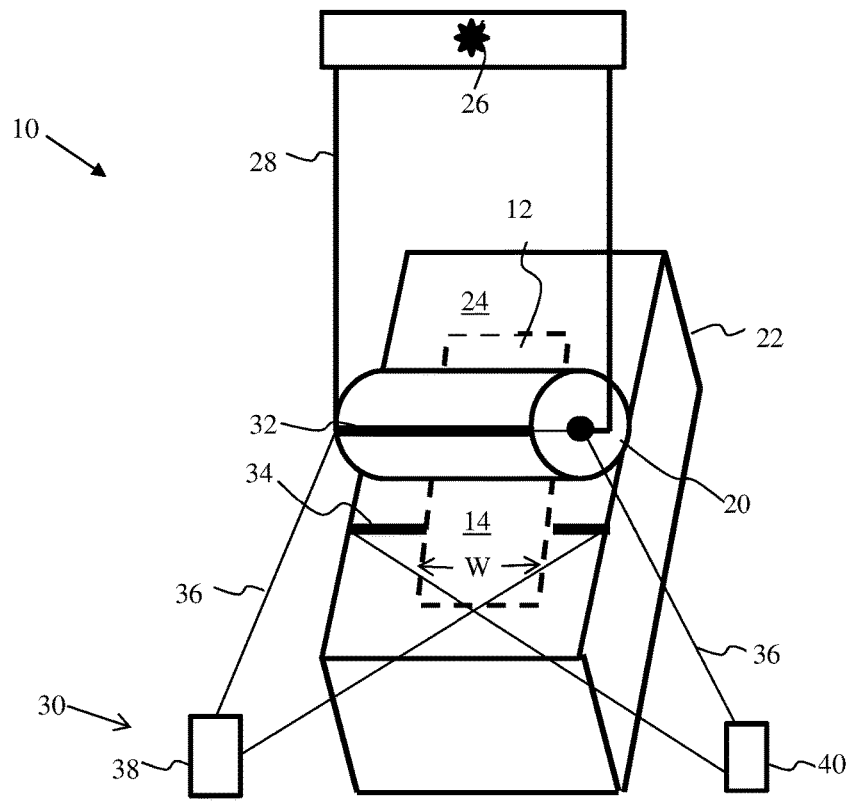
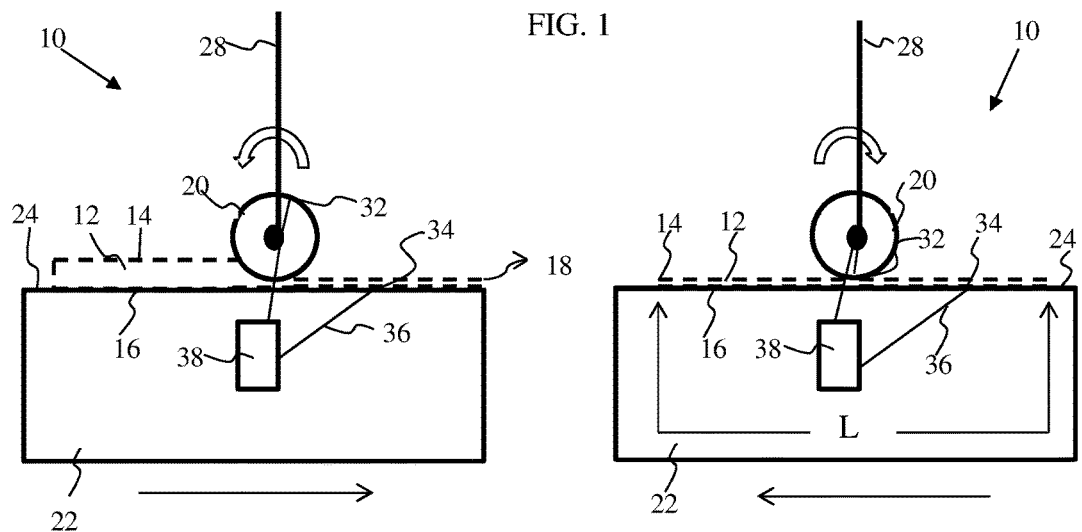
FIG. 1
FIG. 2A            FIG. 2B

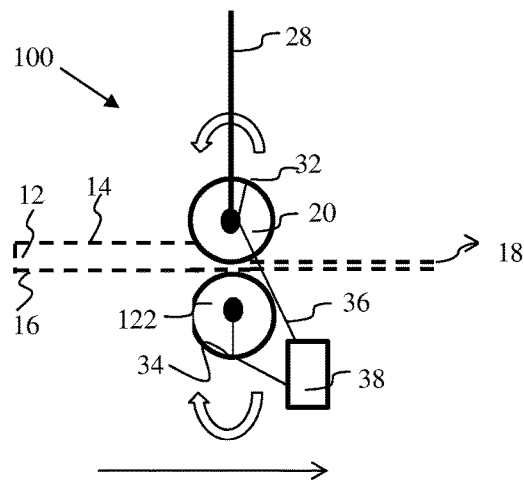
FIG. 3A
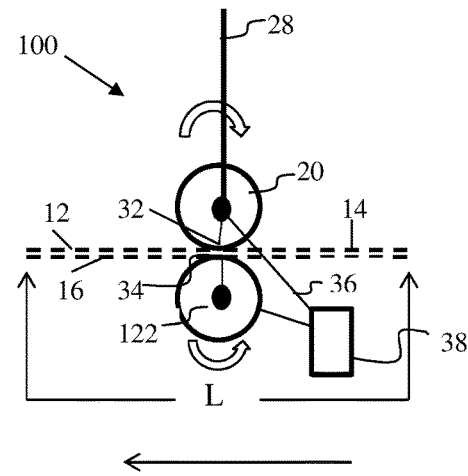
FIG. 3B
FIG. 4
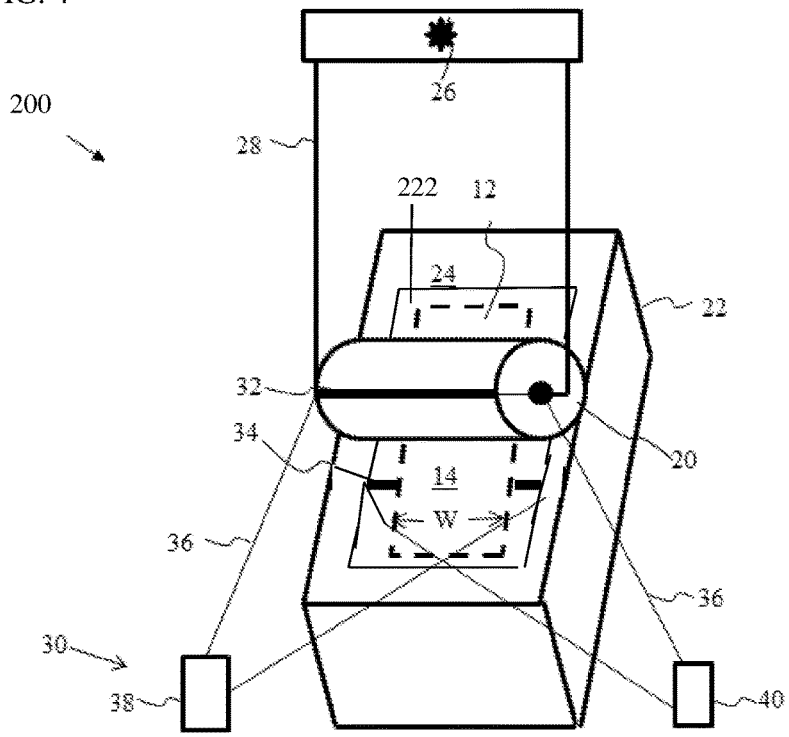

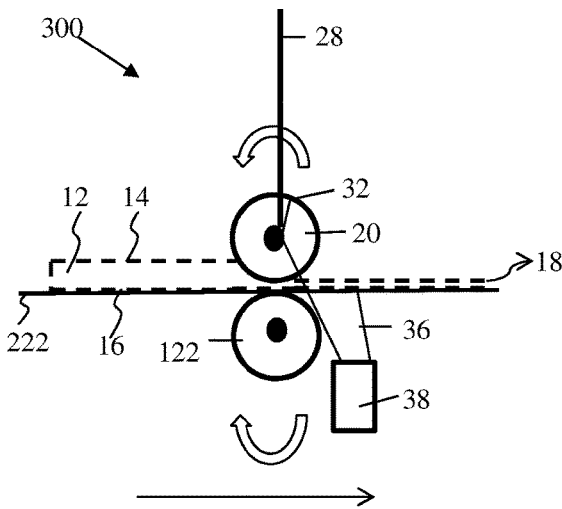
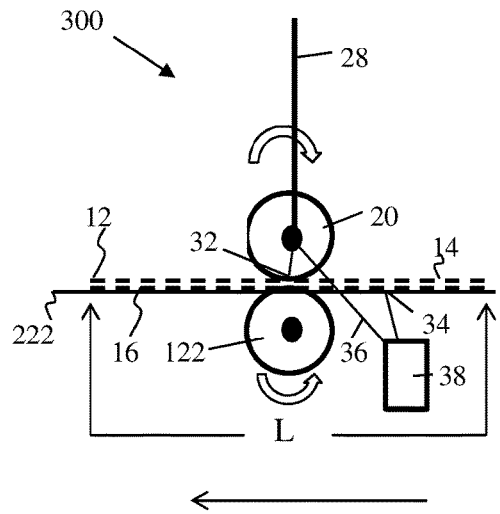
FIG. 5A         FIG. 5B
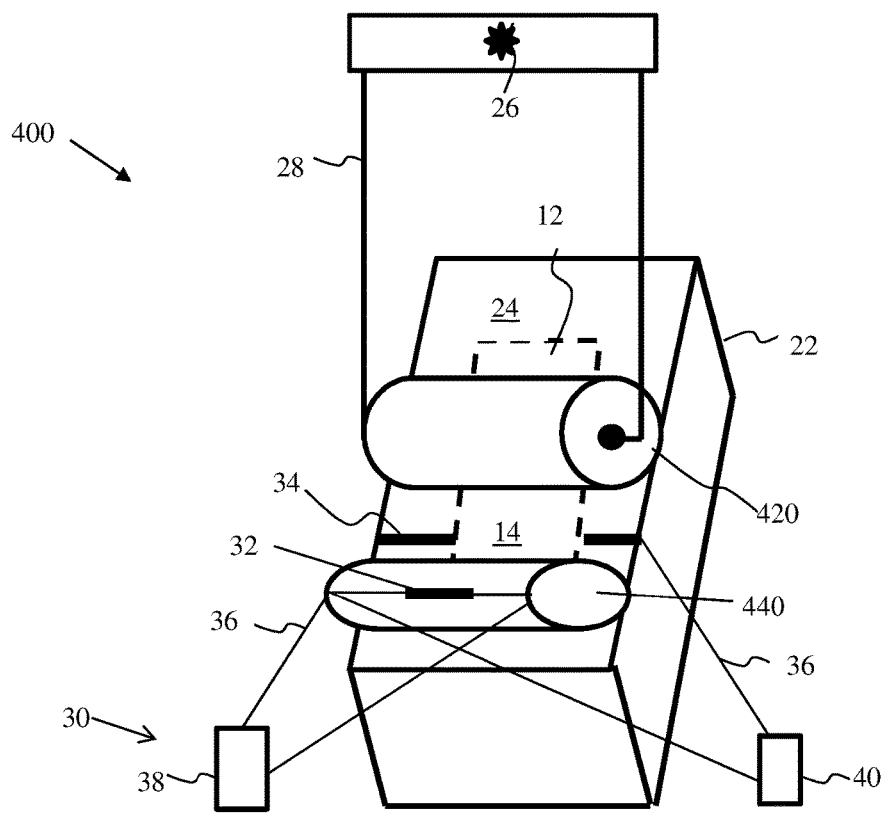
FIG. 6

ROLLING PRESS AND CONDUCTIVITY DETECTOR FOR THE MANUFACTURE OF LITHIUM-ION BATTERY ELECTRODES

TECHNICAL FIELD

This disclosure relates to a rolling press and conductivity detector for the manufacture of lithium-ion battery electrodes.

BACKGROUND

Presses are used for battery electrode preparation to achieve desired parameters such as electrode thickness and porosity. A plate press works through applied force, with the obtained thickness directly related to the applied force. A rolling press enables the desired thickness to be set prior to pressing. Conductivity is an important parameter relating to the porosity of the electrode and is typically tested after the pressed electrode is removed from the press.

SUMMARY

Disclosed herein are embodiments of a rolling press and conductivity detector for the manufacture of lithium-ion battery electrodes. One embodiment of the rolling press for the manufacture of a battery electrode includes a first roller of a non-conductive material, a base of a non-conductive material spaced from the first roller equal to a desired thickness of the battery electrode, and a conductivity detector having a first electrode configured to contact a first side of the battery electrode and a second electrode configured to contact a second side of the battery electrode.

Another embodiment of the rolling press for the manufacture of a battery electrode comprises a first roller of a non-conductive material, a base of a non-conductive material, and a conductivity detector. The conductivity detector comprises a first gold electrode positioned on the first roller and configured to contact a first side of the battery electrode, a second gold electrode positioned on the base and configured to contact a second side of the battery electrode simultaneous with the first roller contacting the first side of the battery electrode, a voltage source connected to the first gold electrode and the second gold electrode; and a current meter connected to the first gold electrode and the second gold electrode. The first roller is configured to rotate in a first direction and in a second direction, the conductivity detector measuring conductivity only while the first roller is rotating in the second direction.

Also disclosed are methods of manufacturing the battery electrode. One such method of manufacturing a battery electrode comprises setting a desired thickness of the battery electrode by setting a gap between a first roller and a base, the first roller and the base made of non-conductive material, feeding the battery electrode through the gap in a first direction to produce the desired thickness, and measuring a conductivity of the battery electrode with a conductivity detector. The conductivity detector comprises a first electrode configured to contact a first side of the battery electrode and a second electrode configured to contact a second side of the battery electrode. Measuring the conductivity occurs when the first electrode and the second gold electrode contact the battery electrode simultaneously.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 1 is a perspective view of an embodiment of the rolling press and conductivity meter as disclosed herein.

FIGS. 2A and 2B are side views of the embodiment of the rolling press and conductivity meter of FIG. 1.

FIGS. 3A and 3B are side views of another embodiment of the rolling press and conductivity meter disclosed herein.

FIG. 4 is a perspective view of yet another embodiment of the rolling press and conductivity meter disclosed herein.

FIGS. 5A and 5B are side views of another embodiment of the rolling press and conductivity meter of FIG. 4.

FIG. 6 is a perspective view of yet another embodiment of the rolling press and conductivity meter disclosed herein.

DETAILED DESCRIPTION

Figure 7:
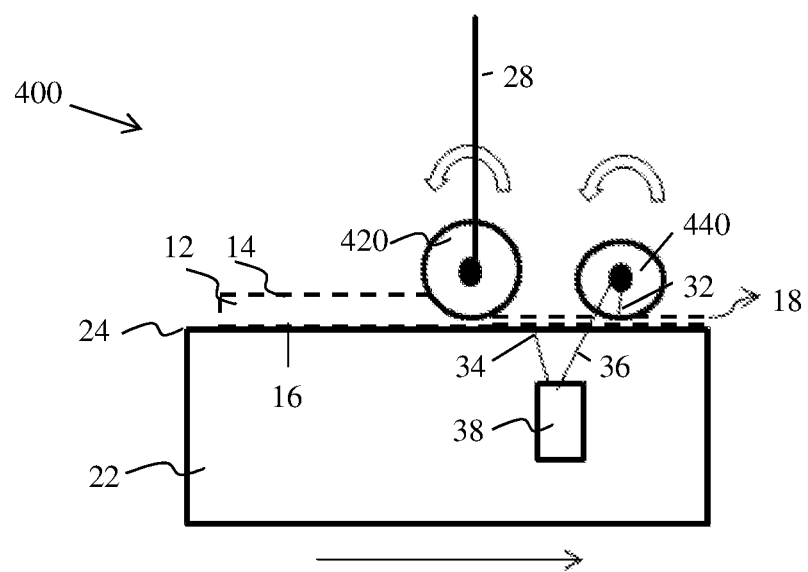
FIG. 7 is a side view of the embodiment of the rolling press and conductivity meter of FIG. 6.

Battery electrodes are conventionally produced by preparing a slurry of cathode or anode active material and layering the slurry onto a current collector. The battery electrode is then pressed to achieve the proper thickness, which relates to the resulting porosity and conductivity of the active material layer. Plate presses use force to achieve the desired thickness. Therefore, a graph of applied force versus obtained thickness is required for each press prior to pressing the battery electrode so that the proper force is used to achieve the desired thickness. The desired thickness is selected in part to provide the desired porosity of the active material layer. Once the battery electrode has been pressed, the battery electrode is connected to a conductivity meter to obtain the resulting conductivity of the active material layer, which corresponds to the resulting porosity.

Rolling presses improve upon plate presses by allowing for the desired thickness to be set between the rollers or the roller and base of the rolling press rather than requiring the use of an applied force versus obtained thickness curve. To further improve upon conventional presses, the inventors developed embodiments of a rolling press and conductivity meter as disclosed herein. In the disclosed embodiments, conductivity can now be obtained by measuring the resistance in the active material layer while pressing the battery electrode in a rolling press, thereby providing an in-situ conductivity test while pressing, measuring the conductivity change with respect to thickness and porosity. In addition, battery electrode processing steps are decreased, resulting in decreased processing time.

Disclosed herein are embodiments of a rolling press and conductivity detector for the manufacture of lithium-ion battery electrodes, shown in FIGS. 1-4. As illustrated in FIGS. 1, 2A and 2B, one embodiment of the rolling press 10 for the manufacture of the battery electrode 12 having a first side 14 and a second side 16 includes a first roller 20, a base 22 spaced from the first roller 20 by a gap 18 equal to a desired thickness of the battery electrode 12, and a conductivity detector 30. The conductivity detector 30 has a first electrode 32 configured to contact the first side 14 of the battery electrode 12 and a second electrode 34 configured to contact the second side 16 of the battery electrode 12.

The first roller 20 and the base are made of a non-conductive material such as porcelain, hard plastic and rubber. The first roller 20 and the base 22 can be formed of metal or another conductive material and covered with a non-conductive material. The first roller 20 and the base 22 can be the same material or different materials.

The base 22 has a substantially planar surface 24 along which the battery electrode 12 is conveyed by rotation of the first roller 20. The gap 18 is set using a knob 26 or other means of adjusting the vertical spacing between the first roller 20 and the base 22. As a non-limiting example, rotating the knob 26 to the right can move the first roller 20 toward the base 22 on telescopic arms 28, decreasing the size of the gap 18, thereby decreasing the resulting thickness of the battery electrode 12. Rotating the knob 26 to the left may move the first roller 20 away from the base 22, increasing the gap 18 and thereby increasing the resulting thickness of the battery electrode 12.

The conductivity controller 30 of the rolling press 10 includes a first electrode 32 configured to contact the first side 14 of the battery electrode 12 and a second electrode 34 configured to contact the second side 16 of the battery electrode 12. As illustrated in FIG. 1, the first electrode 32 is positioned on the surface of the first roller 20 and the second electrode 34 is positioned on the surface 24 of the base 22. The first and second electrodes 32, 34 can be formed of gold, which has a strong resistance to surface oxidation. Other non-limiting examples include silver, copper, iron oxide and carbon. The first and second electrodes 32, 34 can be as small as possible to reduce the amount of electrode material used. As shown, the first and second electrodes 32, 34 can be thin strips that span the width W of the battery electrode 12. Although the first and second electrodes 32, 34 are shown in FIG. 1 to span the width of the first roller 20 and the base 22, this is not necessary. One or both of the first electrode 32 and the second electrode 34 can be shorter than the width W of the battery electrode 12 to remove the potential of shorting the system if the first and second electrodes 32, 34 happen to contact each other. As a non-limiting example of the conductivity meter 30, the first and second electrodes 32, 34 are each connected with wire 36, such as copper wire, to both a voltage source 38 and a current meter 40. Other detectors known to those skilled in the art capable of providing a means to determine conductivity can be used in place of the voltage source and current meter.

As illustrated in FIG. 2A, the battery electrode 12 is introduced to the rolling press 10 to the left of the first roller 20 in this example. The battery electrode 12 is moving in the direction of the straight arrow while the first roller 20 is moving in the direction of the curved arrow. The battery electrode 12 is pressed in FIG. 2A to a thickness that is equal to the gap 18 to which the first roller 20 is set to provide. Once the entire length L of the battery electrode 12 is pressed, the direction of movement changes, with the battery electrode 12 moving in the direction of the straight arrow in FIG. 2B and the first roller 20 reversing its rotational movement. When the movement is reversed, the conductivity detector 30 takes a current measurement when the first electrode 32 is in contact with the first side 14 of the battery electrode 12 and the second electrode 34 is in simultaneous contact with the second side 16 of the battery electrode 12. At that time, a complete circuit is formed with the voltage source 38, current meter 40, wire 36, first and second electrodes 32, 34 and the battery electrode 12. The current through the circuit is measured with the current meter 40, and the current is used to determine resistance using Ohms law. This resistance is converted to conductivity.

Because the circuit is only formed when the first electrode 32 and the second electrode 34 simultaneously contact the battery electrode 12, the second electrode 34 is positioned on the surface 24 of the base 22 so that the battery electrode 12 lays across the second electrode 34 as it is being moved by the first roller 20. In addition, the circumference of the first roller 20 is less than the length L of the battery electrode 12 being pressed to ensure that the first electrode 32 contacts the first side 14 of the battery electrode 12.

FIGS. 3A and 3B are side views of another embodiment of the rolling press 10 of FIG. 1. Like numerals will be used for like elements. The rolling press 100 of FIGS. 3A and 3B has a base roller 122 as a base. The first roller 20 is adjusted to obtain the desired gap as previously described. The base roller 122 is vertically stationary. The base roller 122 rotates in the opposite direction of the first roller 20 to assist in moving the battery electrode 12 through the rollers 20, 122. The battery electrode may be fed from a feed roller, not shown, and gathered on a take up roller, also not shown. The second electrode 34 is positioned on the surface of the base roller 122. The circumference of the base roller 122 is shorter than a length L of the battery electrode. The first roller 20 and the base roller 122 are timed as shown in FIG. 3B, when the movement of the battery electrode 12 has been reversed, so that the first electrode 32 and the second electrode 34 contact the battery electrode 12 simultaneously to complete the circuit to obtain the current measurement needed to determine conductivity.

FIG. 4 illustrates another embodiment of the rolling press 10 of FIG. 1. In FIG. 4, the rolling press 200 positions the second electrode 34 on a non-conductive substrate 222 that moves with the battery electrode 12. The second electrode 34 is wider than the width W of the battery electrode 12, and the battery electrode 12 lays across the second electrode 34 as illustrated. Using the substrate 222 can assist in keeping the base 22 clean. The substrate 222 also may allow for easier replacement of the second electrode 34. It is also contemplated that the substrate 222 be non-moving, essentially placed over the surface 24 of the base 22 and attached thereto. The battery electrode 12 can move over the substrate 222 and second electrode 34 as it would over the surface 24 of the base 22.

FIGS. 5A and 5B illustrate a rolling press 300 using the substrate 222 as described with respect to FIG. 4 but with the use of the base roller 122 rather than the base 22 with the planar surface 24. As with the embodiment illustrated in FIG. 4, the second electrode 34 is on the substrate 222 rather than on the base roller 122, alleviating the need to time the first and second rollers 20, 122 to ensure simultaneous contact of the first and second electrodes 32, 34 with the battery electrode 12. The first roller 20 is adjusted to obtain the desired gas as previously described. The base roller 122 is vertically stationary. The base roller 122 rotates in the opposite direction of the first roller 20 to assist in moving the battery electrode 12 through the rollers 20, 122. The battery electrode may be fed from a feed roller, not shown, and gathered on a take up roller, also not shown.

FIGS. 6 and 7 illustrate yet another embodiment of the rolling press. The rolling press 400 in FIGS. 6 and 7 for the manufacture of the battery electrode 12 includes a first roller 420, a base 22 spaced from the first roller 420 by a gap 18 equal to a desired thickness of the battery electrode 12, and a conductivity detector 30. The rolling press 400 also includes a second roller 440 downstream of the first roller 420. The conductivity detector 30 has a first electrode 32 configured to contact the first side 14 of the battery electrode 12 and a second electrode 34 configured to contact the second side 16 of the battery electrode 12.

The first roller 420, the second roller 440 and the base 22 are made of a non-conductive material such as porcelain, hard plastic and rubber. The first roller 420, the second roller 440 and the base 22 can be formed of metal or another conductive material and covered with a non-conductive material. The first roller 420, second roller 440 and the base 22 can be the same material or different materials.

The base 22 has a substantially planar surface 24 along which the battery electrode 12 is conveyed by rotation of the first roller 420. The gap 18 is set using a knob 26 or other means of adjusting the vertical spacing between the first roller 420 and the base 22. As a non-limiting example, rotating the knob 26 to the right can move the first roller 420 toward the base 22 on telescopic arms 28, decreasing the size of the gap 18, thereby decreasing the resulting thickness of the battery electrode 12. Rotating the knob 26 to the left may move the first roller 420 away from the base 22, increasing the gap 18 and thereby increasing the resulting thickness of the battery electrode 12.

The conductivity controller 30 of the rolling press 400 includes a first electrode 32 configured to contact the first side 14 of the battery electrode 12 and a second electrode 34 configured to contact the second side 16 of the battery electrode 12. As illustrated in FIG. 6, the first electrode 32 is positioned on the surface of the second roller 440 and the second electrode 34 is positioned on the surface 24 of the base 22. The first and second electrodes 32, 34 can be formed of gold, which has a strong resistance to surface oxidation. Other non-limiting examples include silver, copper, iron oxide and carbon. The first and second electrodes 32, 34 can be as small as possible to reduce the amount of electrode material used. As shown, the first and second electrodes 32, 34 can be thin strips that span the width W of the battery electrode 12. One or both of the first electrode 32 and the second electrode 34 can be shorter than the width W of the battery electrode 12 to remove the potential of shorting the system if the first and second electrodes 32, 34 happen to contact each other. In FIG. 6, the first electrode 32 is shorter than a width W of the battery electrode 12. The first and second electrodes 32, 34 are each connected with wire 36, such as copper wire, for example, to both a voltage source 38 and a current meter 40.

In this embodiment of the rolling press 400, both the first roller 420 and the second roller 440 rotate in the same direction as illustrated in FIG. 7. The first roller 420 presses the battery electrode 12 to the set thickness and the second roller 440 measures the current across the pressed battery electrode 12 downstream of the first roller 420 when the circuit is completed, i.e., when the first electrode 32 and the second electrode 34 simultaneously contact the battery electrode 12. Therefore, there is no need to change direction of the rotation of the first roller 420 and the second roller 440, and direction of the battery electrode 12, to obtain conductivity of the pressed battery electrode 12.

The first roller 420 is not restrained in size as the first roller 420 is not supporting the first electrode 32. Rather, the second roller 440 has a circumference that is less than the length L of the battery electrode 12 to ensure the circuit with the conductivity meter 30 is closed. As the second roller 440 does not need to apply pressure to the battery electrode 12, the second roller 440 can roll due to friction with the first side 14 of the battery electrode 12 if desired. As with any embodiment disclosed herein, the battery electrode 12 may be fed from a feed roller, not shown, and gathered on an up-take roller, also not shown.

The substrate 222 described with reference to FIGS. 4, 5A and 5B, supporting the second electrode 34, can be used with this embodiment rather than having the second electrode 34 on the surface 24 of the base 22.

Figure 8:
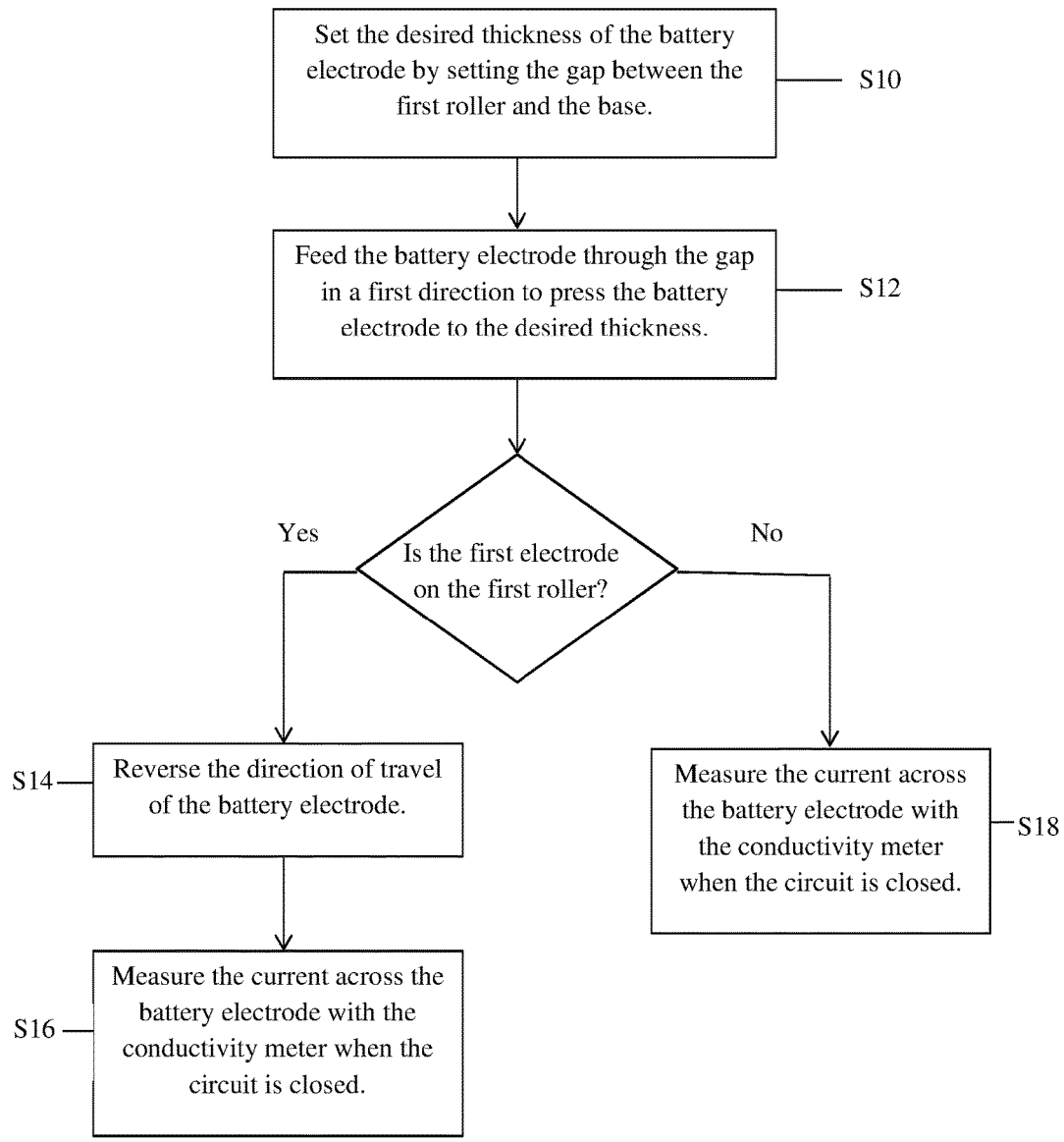
FIG. 8 is a flow diagram of a method of manufacturing the battery electrode using embodiments of the rolling press disclosed herein.

A flow diagram is shown in FIG. 8 illustrating a method of manufacturing the battery electrode 12 described herein. The method comprises setting a desired thickness of the battery electrode 12 by setting the gap 18 between the first roller 20, 420 and the base 22 or base roller 122 in step S10. The battery electrode 12 is fed through the gap 18 in a first direction to produce the desired thickness in step S12.

If the first electrode 32 is on the first roller 20, the process proceeds to step S14, where the direction of travel of the battery electrode 12 is reversed to the second direction. The current across the battery electrode 12 is measured with the conductivity detector 30 in step S16 when the circuit is closed by the first electrode 32, the second electrode 34 and the battery electrode 12.

If the first electrode 32 is not on the first roller 20, then the first electrode is on the second roller 440 as illustrated in FIGS. 6 and 7. The method moves to step S18, where the battery electrode 12 continues in the first direction and the conductivity meter 30 measures current across the battery electrode 12 when the circuit is closed with the first electrode 32 on the second roller 440 and the second electrode 34 on the base 22, base roller 122 or substrate 222.

While the invention has been described in connection with certain embodiments, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A rolling press for the manufacture of a battery electrode, comprising:
   a first roller of a non-conductive material;
   a base of a non-conductive material spaced from the first roller equal to a desired thickness of the battery electrode;
   a conductivity detector comprising:
      a first electrode configured to contact a first side of the battery electrode; and
      a second electrode configured to contact a second side of the battery electrode.

2. The rolling press of claim 1, wherein the first roller is configured to rotate in a first direction and in a second direction, the conductivity detector measuring conductivity only while the first roller is rotating in the second direction.

3. The rolling press of claim 2, wherein the first electrode is a strip of gold formed along a length of the first roller.

4. The rolling press of claim 2, wherein:
   the first electrode is positioned on a rolling surface of the first roller and the second electrode is positioned on the base;
   a circumference of the first roller is less than a length of the battery electrode to be pressed; and
   a width of at least one of the first electrode and the second electrode is shorter than a width of the battery electrode to be pressed.

5. The rolling press of claim 4, wherein the base is a planar stationary surface and the second electrode is a strip of gold across a width of the planar stationary surface.

6. The rolling press of claim 4, wherein:
the base is a second roller positioned opposite the first roller;
the second electrode is positioned on a rolling surface of the second roller; and
a circumference of the second roller is less than a length of the battery electrode to be pressed.

7. The rolling press of claim 4, wherein the second electrode is formed on a surface of a non-conductive substrate configured to hold the battery electrode and move with the battery electrode.

8. The rolling press of claim 1, wherein the conductivity detector further comprises:
a second roller positioned downstream of the first roller, wherein:
the first electrode is positioned on a rolling surface of the second roller and the second electrode is positioned on the base;
a circumference of the second roller is less than a length of the battery electrode to be pressed;
a width of at least one of the first electrode and the second electrode is less than a width of the battery electrode to be pressed;
the first roller is configured to press the battery electrode to a desired thickness; and
the conductivity detector is configured to measure conductivity of the battery electrode after the first roller has pressed the battery electrode and when the first electrode and the second electrode are simultaneously contacting the battery electrode.

9. The rolling press of claim 1, wherein the conductivity detector further comprises:
a voltage source connected to the first electrode and the second electrode; and
a current meter connected to the first electrode and the second electrode.

10. A rolling press for the manufacture of a battery electrode, comprising:
a first roller of a non-conductive material;
a base of a non-conductive material;
a conductivity detector comprising:
a first gold electrode positioned on the first roller and configured to contact a first side of the battery electrode;
a second gold electrode positioned on the base and configured to contact a second side of the battery electrode simultaneous with the first roller contacting the first side of the battery electrode;
a voltage source connected to the first gold electrode and the second gold electrode; and
a current meter connected to the first gold electrode and the second gold electrode, wherein the first roller is configured to rotate in a first direction and in a second direction, the conductivity detector measuring conductivity only while the first roller is rotating in the second direction.

11. The rolling press of claim 10, wherein:
a circumference of the first roller is less than a length of the battery electrode to be pressed; and
a width of at least one of the first gold electrode and the second gold electrode is less than a width of the battery electrode to be pressed.

12. The rolling press of claim 10, wherein the base is a planar stationary surface and the second gold electrode is a strip of gold across at least a portion of a width of the planar stationary surface.

* * * * *